US007215985B2

(12) United States Patent
Petersen et al.

(10) Patent No.: US 7,215,985 B2
(45) Date of Patent: May 8, 2007

(54) OXIMETER CROSS-TALK REDUCTION

(75) Inventors: Ethan Petersen, Castro Valley, CA (US); Bradford B. Chew, San Ramon, CA (US); William Shea, Livermore, CA (US)

(73) Assignee: Nellcor Puritain Bennett Inc., Pleasanton, CA (US)

( * ) Notice: Subject to any disclaimer, the term of this patent is extended or adjusted under 35 U.S.C. 154(b) by 364 days.

(21) Appl. No.: 10/787,541

(22) Filed: Feb. 25, 2004

(65) Prior Publication Data

US 2005/0187452 A1  Aug. 25, 2005

(51) Int. Cl.
*A61B 5/00* (2006.01)

(52) U.S. Cl. ......................... 600/336; 600/323

(58) Field of Classification Search ................ 600/322, 600/323, 331, 336; 702/189
See application file for complete search history.

(56) References Cited

U.S. PATENT DOCUMENTS

| | | | |
|---|---|---|---|
| 4,802,486 A | 2/1989 | Goodman et al. | |
| 4,911,167 A | 3/1990 | Corenman et al. | |
| 4,928,692 A | 5/1990 | Goodman et al. | |
| 4,934,372 A | 6/1990 | Corenman et al. | |
| 4,942,877 A | 7/1990 | Sakai et al. | |
| 5,351,685 A | 10/1994 | Potratz | |
| 5,368,026 A | 11/1994 | Swedlow et al. | |
| 5,662,106 A | 9/1997 | Swedlow et al. | |
| 5,713,355 A | 2/1998 | Richardson et al. | |
| 5,746,697 A | 5/1998 | Swedlow et al. | |
| 5,803,910 A | 9/1998 | Potratz | |
| 5,921,921 A | 7/1999 | Potratz et al. | |
| 5,924,979 A | 7/1999 | Swedlow et al. | |
| 5,995,858 A | 11/1999 | Kinast | |
| 6,226,539 B1 | 5/2001 | Potratz | |
| 6,505,133 B1 | 1/2003 | Hanna et al. | |
| 2001/0002206 A1 | 5/2001 | Diab et al. | |
| 2003/0028357 A1* | 2/2003 | Norris et al. | ............... 702/189 |

* cited by examiner

*Primary Examiner*—Eric Winakur
*Assistant Examiner*—Etsub Berhanu
(74) *Attorney, Agent, or Firm*—Fletcher Yoder PC

(57) ABSTRACT

A method and apparatus for reducing cross-talk in an oximeter. The oximeter includes a band pass filter. The amount of cross-talk through the band pass filter is estimated. Based on this estimate, the corner frequencies of the band pass filter are adjusted when it is designed to minimize the cross-talk. In one embodiment, a calibration mode is performed when a sensor is attached to the oximeter. In the calibration mode, the signals are measured with first only the red LED on and then with only the IR LED on. Any signal measured in the off channel is assumed to be a result of cross-talk from the other channel. The magnitude of the cross-talk is determined as a percentage, and subsequently the percentage is multiplied by the actual signal and subtracted from the other LED signal as cross-talk compensation.

19 Claims, 4 Drawing Sheets

OXIMETER CROSS-TALK REDUCTION

BACKGROUND OF THE INVENTION

The present invention relates to oximeters, and in particular to methods for reducing cross-talk between red and IR signals in pulse oximeters.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light at various wavelengths in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

A typical pulse oximeter will alternately illuminate the patient with red and infrared light to obtain two different detector signals. One of the issues with each signal, for the red and infrared (IR), is cross-talk. For example, the red signal, after filtering, will still be tailing off when the IR LED is turned on, and vice-versa. Typically pulse oximeter circuits include such filters to filter out noise before demodulating, such as the 50 or 60 Hz ambient light from fluorescent or other lights, or electrical interference. Such filtering can result in crosstalk when the filtering spreads out the red and IR pulses so they overlap.

One approach for dealing with cross-talk in the form of phase distortion, as opposed to the amplitude distortion the present invention addresses, is shown in U.S. Pat. No. 5,995,858. This patent shows an approach where the same signal drives the red and IR at opposite phases, giving a phase offset problem. This patent deals with a phase error in the response of the band pass filter of a reference signal causing cross-talk of red into IR and vice versa. In order to minimize or compensate for this phase error, the oximeter is operated with only the IR LED active, and then only with the red LED active. From this, a correction constant is determined that is used in the equation for determining oxygen saturation.

BRIEF SUMMARY OF THE INVENTION

The present invention provides a method and apparatus for reducing cross-talk in an oximeter. The oximeter includes a band pass filter. The amount of cross-talk through the band pass filter is estimated. Based on this estimate, the corner frequencies of the band pass filter are adjusted to minimize the cross-talk.

In one embodiment, the band pass filter is a hardware filter, and the corner frequencies are adjusted in the design and selection of the appropriate resistors and capacitors. In another embodiment, the band pass filter is in hardware, and the frequencies can be adjusted during operation or calibration.

In another embodiment, the present invention also includes a calibration mode which is performed when a sensor is attached to the oximeter. In the calibration mode, the signals are measured with first only the red LED on and then with only the IR LED on. Any signal measured in the off channel is assumed to be a result of cross-talk from the other channel. The effect is linear, enabling it to be compensated for in software. The magnitude of the cross-talk is determined as a percentage, and subsequently the percentage is multiplied by the actual signal and subtracted from the other LED signal as cross-talk compensation.

For a further understanding of the nature and advantages of the invention, reference should be made to the following description taken in conjunction with the accompanying drawings.

DETAILED DESCRIPTION OF THE INVENTION

Overall System

Figure 1:
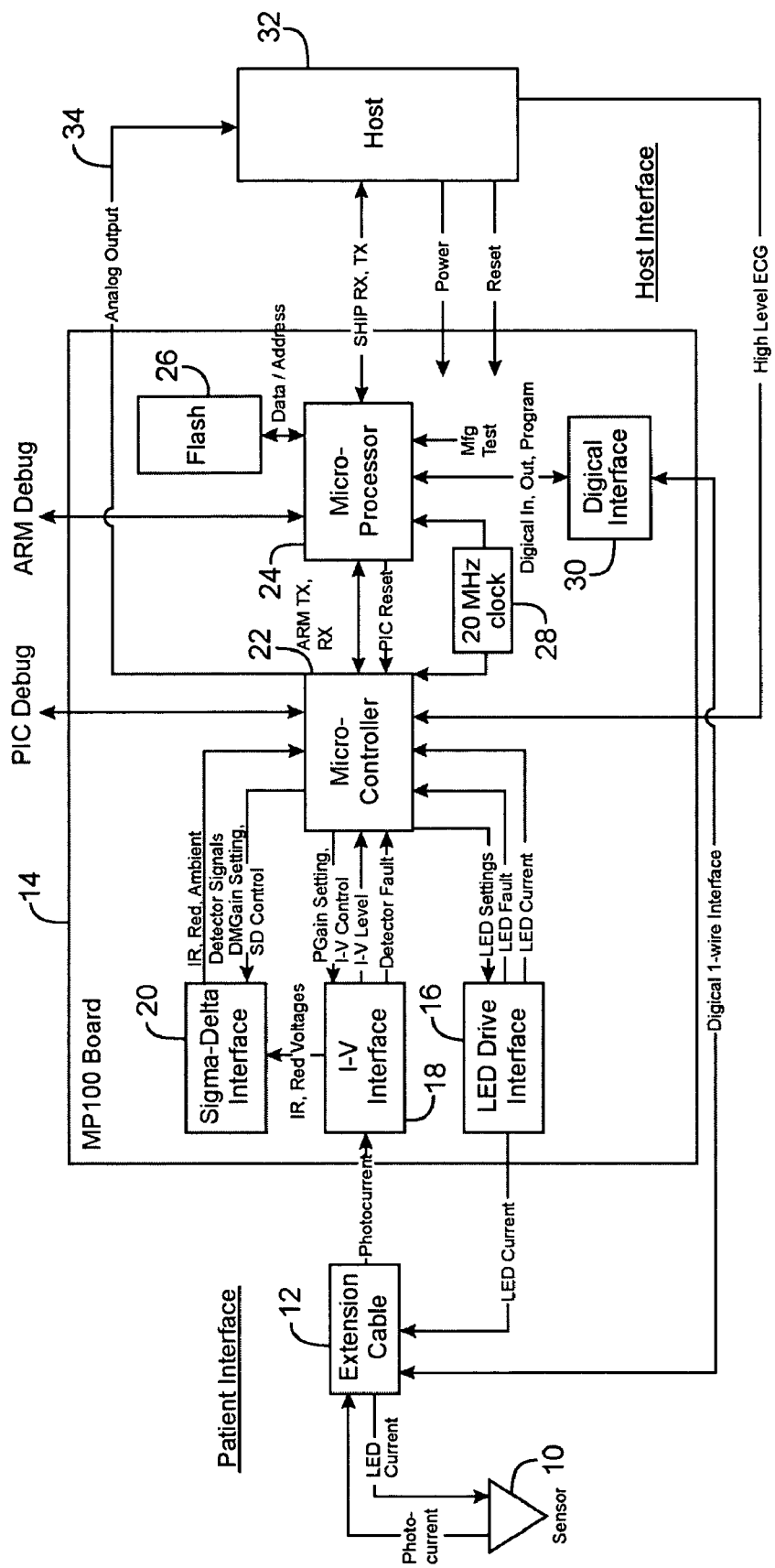
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22. Microcontroller 22 includes flash memory for a program, and SRAM memory for data. The processor also includes a microprocessor chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

Bandpass Filter

Figure 2:
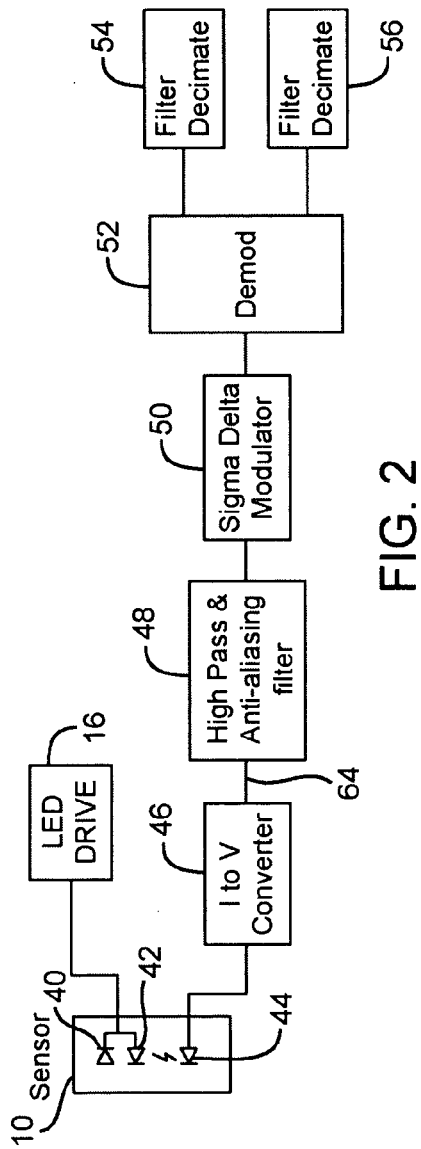
FIG. 2 is a block diagram of a portion of the circuit of FIG. 1 illustrating the placement of a filter according to the present invention.

FIG. 2 is a block diagram illustrating the location of the filter according to an embodiment of the invention. Shown is a sensor 10 that is driven by an LED drive circuit 16. The LED drive circuit 16 alternately drives an IR LED 40 and a red LED 42. A photodetector 44 provides a signal to a current-to-voltage (I-V converter 46). The voltage signal is provided to high pass signal and anti-aliasing filter 48. This block includes the band pass filter according to an embodiment of the invention. The output signal is then provided to a sigma-delta modulator 50. The output of sigma-delta modulator 50 is provided to a demodulator 52, which is then provided to filtering and decimating blocks 54 and 56.

Figure 3:
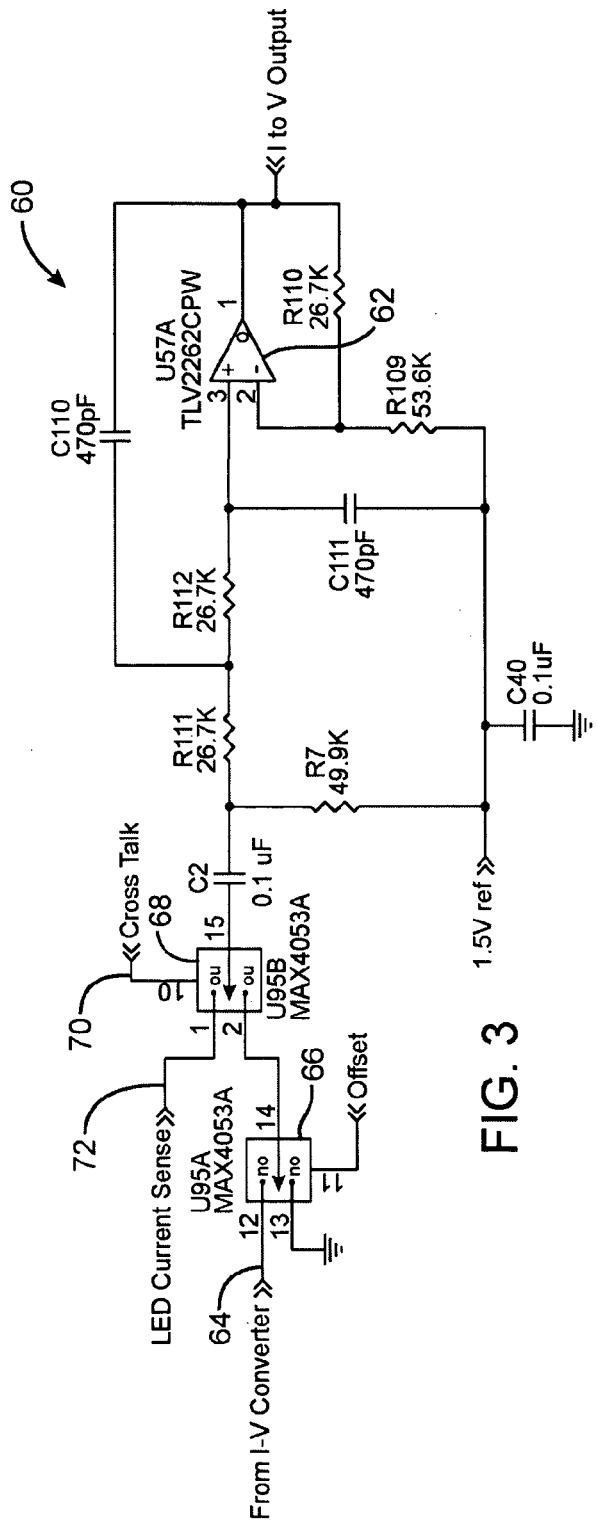
FIG. 3 is a circuit diagram of a band pass filter according to an embodiment of the invention.

FIG. 3 illustrates a band pass filter 60 according to an embodiment of the invention. The filter includes an amplifier 62 and a resistor and capacitor circuit comprising capacitors C2, C110, C111, and C40 and resistors R7, R111, R112, R110, and R109. An input to this circuit is provided from I-V converter 46 along a line 64 to a first switch 66 for an offset correction not relevant to the present invention. The signal is then provided to a second switch 68, which is used for a calibration mode according to the present invention. A cross-talk control signal 70 couples the switch to an LED current sense line 72 for calibration mode.

Design of Bandpass Filter

In the design and manufacture of the band pass filter of FIG. 3, the corner frequencies are adjusted by varying the capacitor and resistor values to offset and minimize the cross-talk effect. The corner frequencies are the high pass and low pass ends of the band pass filter, which is in place to filter out ambient interferences.

There is a major trade off involved in the design of the band pass filter. It is desirable to have the filter corners as close to the modulation frequency as possible. Raising the frequency of the high pass corner makes the filter better able to reject any AC portion of ambient light. Typically in the US, fluorescent lights have strong AC component at 120 Hz and the harmonics of 120 Hz. It is desirable to filter this out of the signal. Lowering the cut off frequency of the low pass filter limits the high frequency noise from the I-V converter, and provides some anti-aliasing to keep ambient noise out of the system.

However, any filtering spreads out the signal in the time domain, for example some of the IR pulse will leak into the dark pulse following it. This has two drawbacks. The first is cross-talk where the IR signal "leaks" into the red signal, and vice versa. The second is an offset resulting from a transient that occurs due to capacitances in the patient cable between the LED wires and the detector wires. When this transient is filtered, part of it leaks into the sampled part of the signal causing an offset. Both of these effects get worse as the corners of the filters are pulled closer to the modulation frequency.

Figure 4:
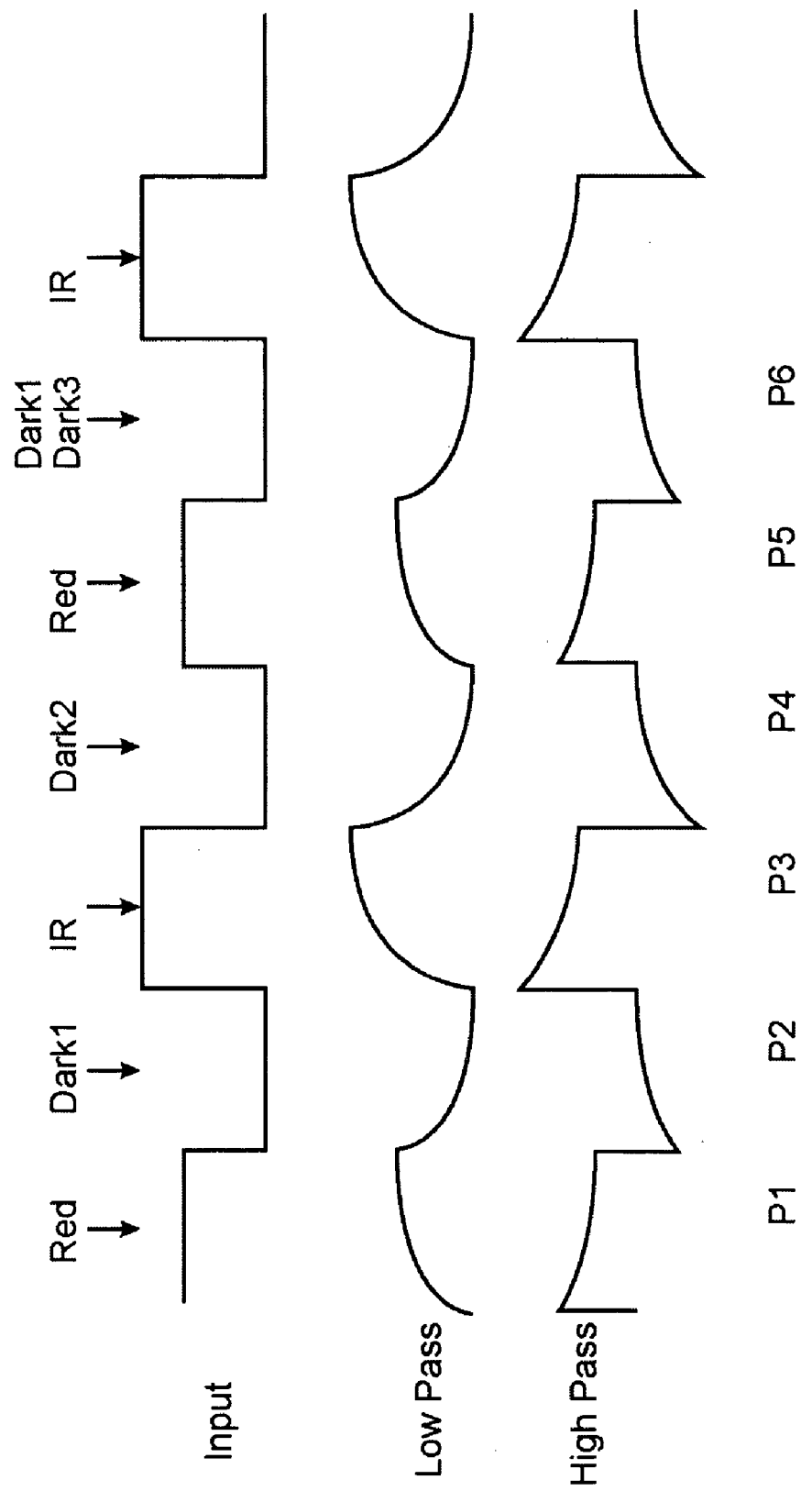
FIG. 4 is a timing diagram illustrating the low and high pass filtering effects on the red and IR signals according to an embodiment of the invention.

Tuning the band pass filter to optimize for cross-talk is done when it is designed by adjusting the high pass filter corner and the low pass corner to force the cross-talk to be zero. The size of the Red pulse is measured by comparing the sample P5 (see FIG. 4) to the samples taken in the dark states P4 and P6.

$$Red = P5 - \frac{P4 + P6}{2}$$

Since the signal from the IR pulse is still decaying in the Dark2 time period, the P4 sample will be higher due to the low pass response and the lower due to the high pass response. The effect of the IR pulse on P4 will affect the size of the measured red signal. This is a cause of cross-talk where the IR signal leaks into the Red signal and vice versa.

This effect is minimized if the filter is a band pass, with both high pass and low pass effects. The effect of the high pass filtering compensates for the effect of the low pass filtering.

Figure 5:
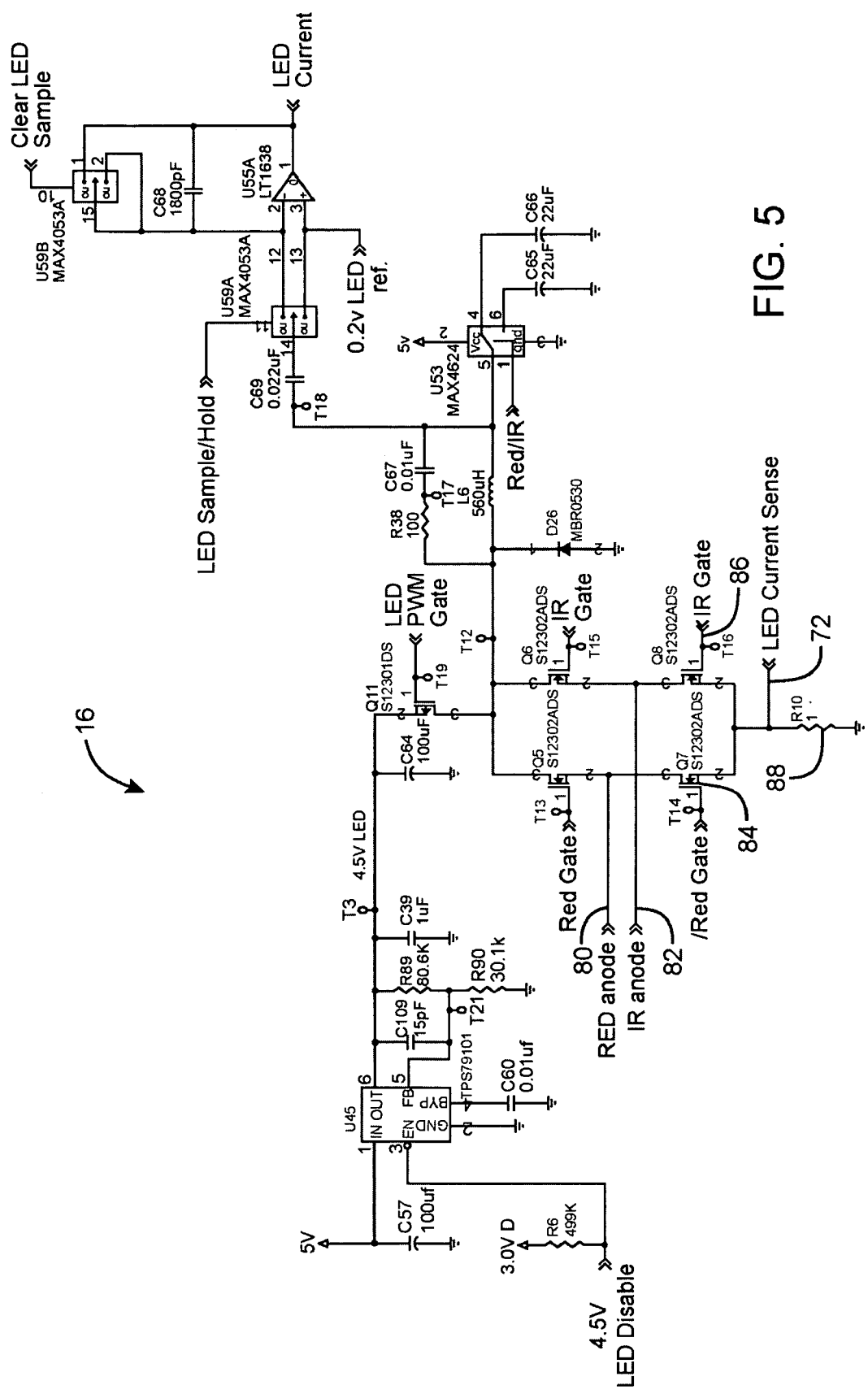
FIG. 5 is a circuit diagram illustrating an embodiment of a LED drive circuit including the circuit connections for the calibration mode according to an embodiment of the invention.

Thus, the corners are adjusted so that the high pass and low pass signals shown in FIG. 5 are adjusted so that the effect of the high pass filtering compensates for the effect of the low pass filtering to minimize cross-talk. The low pass filter causes a positive cross-talk, and the high pass filter causes an offsetting negative cross-talk.

In one embodiment, the band pass filter consists of an RC high pass followed by a Salen-Key low pass configured as a second order Butterworth filter. The impedance of the RC high pass section will have an effect on the transfer function of the Salen-Key circuit, however this effect is negligible if capacitance C2 is much larger than C110 and C111. The high pass filter cut off frequency is 32 Hz., and the low pass filter cut off frequency is 12.7 kHz.

Calibration

In addition to designing the hardware of the band pass filter to reduce cross-talk, a calibration mode allows a further correction for cross-talk using a cross-talk calibration test. A subtle cross-talk effect arises from the filtering in the circuit causing light and dark pulses to spread out into each other in the time domain. Fortunately the effects from the band pass filter are linear and measurable, and so can be compensated for in software. Since this is the result of the filtering, the magnitude of the effect is known ahead of time. A constant is used to subtract the effects of the IR signal from the Red signal and vice versa:

Red'=Red−IR*$K$cross

IR'=IR−Red*$K$cross

FIG. 5 is a circuit diagram of an embodiment of LED drive circuit 16 of FIG. 2. Included in the circuit are a connection to the red LED on a line 80, and a connection to the IR LED on a line 82. These are provided through MOSFET transistors 84 and 86 to a 1 ohm resistor 88. In the calibration mode, the LED current sense signal on line 72 is taken from the current through this 1 ohm resistor with line 72 of FIG. 5 connected to line 72 of FIG. 3 as an input through switch 68 to the band pass filter.

In addition to designing the hardware of the band pass filter to reduce cross-talk, the connection of line 72 in FIG. 5 during a calibration mode allows a further correction for cross-talk using a cross-talk calibration test.

While doing the cross-talk test, most of the analog circuits on the board are used and so this is a good test to check the integrity of the analog hardware. This test connects the 1Ω current sense resistor 88 to the input to the band pass filter. This way a fixed LED current can inject a signal into the signal acquisition circuits. This allows the operation of the LED drive 16, the band pass filter 60 and the sigma-delta modulator 50 to be verified. In addition, measuring the LED current using the 1Ω resistor allows the LED's current sense circuit to be calibrated more accurately than the 10% tolerance capacitors in the circuit would ordinarily allow.

Thus, during the calibration mode, current is shunted into the current sense input from the LED drive current. The only analog circuitry not being used is the photodetector and the I-V converter. In a preferred embodiment, whenever a sensor is connected, this is detected and the software automatically does the cross-talk calibration test.

A 50% drive signal is applied to the LEDs during the calibration circuit to give a sufficiently large signal without going to full range and risking too high of a signal being provided. Alternately, other percentages of the drive current could be used.

The following steps are performed:
1) Set IR LED to 50%, Red LED to 0; then measure the 0 red signal;
2) Set Red LED to 50%, IR LED to 0; then measure the 0 IR signal.

Subsequently, during actual operation, the red cross-talk effect is determined by multiplying the percentage cross-talk times the red signal, and then it is subtracted from the IR signal. The corresponding action is done for the red signal.

As will be understood by those of skill in the art, the present invention could be embodied in other specific forms without departing from the essential characteristic thereof. For example, the drive current could be obtained in a different manner and a different design could be used for the band pass filter. Alternately, the band pass filter could be used alone, without the software calibration added. Accordingly, the foregoing description is intended to be illustrative, but not limiting, on the scope of the invention which is set forth in the following claims.

What is claimed is:

1. A method for reducing cross-talk in an oximeter, comprising:
   providing a signal corresponding to an oximeter sensor signal, wherein the signal comprises a time division multiplexed signal;
   applying the signal to a band pass filter, wherein the band pass filter is a hardware band pass filter and is coupled to the output of a current-to-voltage converter in the oximeter;
   estimating an amount of cross-talk of the signal through the band pass filter;
   adjusting the corner frequencies of the band pass filter to minimize the cross-talk;
   measuring an amount of remaining cross-talk through the hardware band pass filter after the adjusting; and
   minimizing the remaining cross-talk by compensation in software of a digitized signal from the hardware band pass filter.

2. The method of claim 1 wherein the measuring comprises:
   measuring a current from a red LED with no current provided to an IR LED; and
   measuring a current from the IR LED with no current provided to the red LED.

3. The method of claim 2 further comprising:
   in a calibration mode:
     measuring an IR cross-talk signal obtained during an IR LED period, the IR cross-talk signal corresponding to cross-talk from a signal from the red LED;
     comparing said IR cross-talk signal to the current from the IR LED to determine an IR cross-talk percentage;
     measuring a red cross-talk signal obtained during a red LED period, the signal corresponding to cross-talk from a signal from the IR LED;
     comparing the red cross-talk signal to the current from the red LED to determine a red cross-talk percentage;
   during normal operation of the oximeter:
     multiplying the IR cross-talk percentage in software by a detected IR signal to generate an IR cross-talk value, and subtracting the IR cross-talk value from a detected red signal; and
     multiplying the red cross-talk percentage in software by a detected red signal to generate a red cross-talk value, and subtracting the red cross-talk value from the detected IR signal.

4. A method for compensating for cross-talk in an oximeter, comprising:
   providing a signal corresponding to an oximeter sensor signal;
   applying the oximeter sensor signal to a hardware band pass filter, wherein the hardware band pass filter is coupled to the output of a current-to-voltage converter in the oximeter;
   estimating an amount of cross-talk of: the oximeter signal through the band pass filter adjusting the corner frequencies of the band pass filter to minimize the cross-talk;
   in a calibration mode:
     measuring an IR cross-talk signal obtained during an IR LED period, the IR cross-talk signal corresponding to cross-talk from a signal from the red LED;
     comparing the IR cross-talk signal to the current from the IR LED to determine an IR cross-talk percentage;
     measuring a red cross-talk signal obtained during a red LED period, the red cross-talk signal corresponding to cross-talk from a signal from the IR LED;
     comparing the red cross-talk signal to the current from the red LED to determine a red cross-talk percentage;
   during normal operation of the oximeter:
     multiplying the IR cross-talk percentage in software by a detected IR signal to generate an IR cross-talk value, and subtracting the IR cross-talk value from a detected red signal; and
     multiplying the red cross-talk percentage in software by a detected red signal to generate a red cross-talk value, and subtracting the red cross-talk value from the detected IR signal.

5. An oximeter with reduced cross-talk comprising:
   an oximeter sensor input;
   a current to voltage converter coupled to oximeter sensor input;
   a band pass filter coupled to said current to voltage converter, the band pass filter having corner frequencies adjusted to minimize cross-talk;
   a test circuit configured to providing a test signal to the band pass filter;
   a memory storing a program configured to operate the test circuit to estimate an amount of remaining cross-talk and determining red and IR cross-talk compensation factors to be used in software during normal operation of oximeter;
   an analog-to-digital converter coupled to the band pass filter to convert a detected signal into a digitized detector signal, wherein the detected signal comprises multiple signals distinguishable in a time domain; and
   a processor coupled to the analog-to-digital converter to manipulate the digitized detector signal and calculate oxygen saturation.

6. The oximeter of claim 5 wherein the test circuit comprises:
   a resistor;
   a switching circuit configured to alternately couple the resistor to red and IR LEDs; and
   a switch configured to couple the resistor to the band pass filter.

7. An oximeter with reduced cross-talk comprising:
   an oximeter sensor input;
   a current to voltage converter coupled to the oximeter sensor input;

a band pass filter coupled to the current to voltage converter, the band pass filter having corner frequencies adjusted to minimize cross-talk;

an analog-to-digital converter coupled to the band pass filter to convert a detected signal into a digitized detector signal;

a processor coupled to the analog-to-digital converter to manipulate a the digitized detector signal and calculate oxygen saturation;

a test circuit configured to provide a test signal to the band pass filter;

a memory storing a program configured to operate the test circuit to estimate an amount of remaining cross-talk and determine red and IR cross-talk compensation factors to be used in software during normal operation of the oximeter;

wherein the program includes computer readable code configured to:

in a calibration mode:

measure an IR cross-talk signal obtained during an IR LED period, the IR cross-talk signal corresponding to cross-talk from a red LED signal;

compare the IR cross-talk signal to the current from an IR LED to determine an IR cross-talk percentage;

measure a red cross-talk signal obtained during a red LED period, the red cross-talk signal corresponding to cross-talk from an IR LED signal;

compare the red cross-talk signal to the current from a red LED to determine a red cross-talk percentage;

during normal operation of the oximeter and:

multiply the IR cross-talk percentage in software by a detected IR signal to generate an IR cross-talk value, and subtract the IR cross-talk value from a detected red signal; and multiply the red cross-talk percentage in software by a detected red signal to generate a red cross-talk value, and subtract the red cross-talk value from the detected IR signal.

8. A method for compensating for cross-talk in an oximeter using a calibration mode, comprising:

providing detector signals corresponding to first and second light emitter wavelengths;

measuring a first cross-talk signal obtained during a first period corresponding to the first light emitter wavelength, the first cross-talk signal corresponding to cross-talk from a signal from the second light emitter wavelength;

comparing the first cross-talk signal to a current from the detector corresponding to a signal of the first light emitter wavelength to determine a first cross-talk percentage;

measuring a second cross-talk signal obtained during a second period corresponding to the second light emitter wavelength, the second cross-talk signal corresponding to cross-talk from a signal from the first light emitter wavelength;

comparing the second cross-talk signal to the current from the detector corresponding to a signal of the second light emitter wavelength to determine a second cross-talk percentage;

during normal operation of the oximeter, multiplying the first cross-talk percentage in software by a detected first wavelength signal to generate a first cross-talk value, and subtracting the first cross-talk value from a detected second wavelength signal; and during normal operation of the oximeter, multiplying the second cross-talk percentage in software by a detected second wavelength signal to generate a second cross-talk value, and subtracting the second cross-talk value from a detected first wavelength signal.

9. The method of claim 8 wherein the first wavelength is red and the second wavelength is IR.

10. An oximeter with reduced cross-talk comprising:

an oximeter sensor input configured to provide a detected signal;

an analog-to-digital converter configured to convert the detected signal into a digitized detector signal;

a processor coupled to the analog-to-digital converter to manipulate the digitized detector signal and calculate oxygen saturation;

a test circuit configured to provide a test signal;

a memory storing a program configured to operate the test circuit to estimate an amount of remaining cross-talk and determine first and second cross-talk compensation factors to be used in software during normal operation of the oximeter;

wherein the program includes computer readable code configured to:

provide detector signals corresponding to first and second light emitter wavelengths;

measure a first cross-talk signal obtained during a first period corresponding to the first light emitter wavelength, the first cross-talk signal corresponding to cross-talk from a signal from the second light emitter wavelength;

compare the first cross-talk signal to a current from the sensor corresponding to a signal of the first wavelength to determine a first cross-talk percentage;

measure a second cross-talk signal obtained during a second period corresponding to the second light emitter wavelength, the second cross-talk signal corresponding to cross-talk from a signal from the first light emitter wavelength;

compare the second cross-talk signal to the current from the sensor corresponding to a signal of the first wavelength to determine a second cross-talk percentage;

during normal operation of the oximeter, multiply the first cross-talk percentage in software by a detected first wavelength signal to generate a first cross-talk value, and subtract the first cross-talk value from a detected second wavelength signal; and during normal operation of the oximeter, multiply the second cross-talk percentage in software by a detected second wavelength signal to generate a second cross-talk value, and subtract the second cross-talk value from a detected first wavelength signal.

11. The oximeter of claim 10 wherein the first wavelength is red and the second wavelength is IR.

12. A system for determining physiological parameters comprising:

a photoelectric sensor configured to generate a time division multiplexed (TDM) signal having a plurality of signal portions in response to a plurality of wavelengths of electromagnetic energy;

a monitor coupled to the sensor and configured to receive the TDM signal, the monitor comprising:

a band-pass filter having corner frequencies adjusted to minimize cross-talk between the signal portions of the TDM signal;

a test circuit configured to provide a test signal to the band-pass filter;

a memory storing a program configured to operate the test circuit to estimate an amount of remaining cross-talk and determine cross-talk compensation factors for each of the signal portions of the TDM signal, wherein the cross-talk compensation factors are to be used in software during normal operation of the monitor;

an analog-to-digital converter coupled to the band-pass filter to convert the TDM signal into a digital signal; and a processor coupled to the analog-to-digital converter to manipulate the digital signal and calculate physiological parameters.

13. The system of claim 12 wherein the plurality of wavelengths of electromagnetic energy comprises a plurality of infrared wavelengths.

14. The system of claim 12 wherein the analog-to-digital converter comprises a sigma-delta modulator.

15. The system of claim 12 wherein the test circuit comprises:

a resistor;

a switching circuit configured to alternately couple the resistor to a plurality of emitters operating in the infrared range of the electromagnetic spectrum; and a switch configured to couple the resistor to the band-pass filter.

16. A cross-talk compensation method for a system configured to determine physiological parameters comprising:

providing a plurality of signals, wherein each of the plurality of signals corresponds to a different wavelength of electromagnetic energy and each of the plurality of signals occupies a unique time period;

determining a plurality of crosstalk constants corresponding to each of the unique time periods for each of the plurality of signals, wherein the plurality of crosstalk constants represents the amount of crosstalk present during the unique time period; and during operation, using the plurality of crosstalk constants to compensate for crosstalk in measurements of the plurality of signals.

17. The method of claim 16 wherein at least a portion of the plurality of signals are IR signals.

18. The method of claim 16 wherein determining a plurality of crosstalk constants comprises implementing a calibration mode, wherein implementing the calibration mode comprises:

measuring a plurality of crosstalk signals during each of the unique time periods, wherein measuring the plurality of crosstalk signals comprises measuring the plurality of signals except for one of the plurality of signals for which the unique time period corresponds.

19. The method of claim 18 wherein using the crosstalk constants to compensate for crosstalk in measurements of the plurality of signals comprises:

measuring each of the plurality of signals; and for each unique time period, multiplying the plurality of signals with a corresponding crosstalk signal to determine the plurality of crosstalk constants, wherein if there is a plurality of signals contributing to the crosstalk, each of the crosstalk constants for the plurality of signals for that unique time period is summed; and subtracting one of the plurality of crosstalk constants for which the unique time period corresponds from the one of the plurality of signals for which the unique time period corresponds.

* * * * *